United States Patent [19]

Rowan et al.

[11] 4,360,438
[45] Nov. 23, 1982

[54] ORGANOMOLYBDENUM BASED ADDITIVES AND LUBRICATING COMPOSITIONS CONTAINING SAME

[75] Inventors: Eugene V. Rowan, Rowayton; Homer H. Farmer, Westport, both of Conn.

[73] Assignee: R. T. Vanderbilt Company, Inc., Norwalk, Conn.

[21] Appl. No.: 157,135

[22] Filed: Jun. 6, 1980

[51] Int. Cl.$^3$ .................. C10M 1/54; C10M 3/48; C10M 5/28
[52] U.S. Cl. .................. 252/33.6; 252/46.4; 252/41.5
[58] Field of Search ............................ 252/33.6

[56] References Cited

U.S. PATENT DOCUMENTS

| | | | |
|---|---|---|---|
| 2,179,066 | 11/1930 | Smith | 260/327 |
| 2,786,866 | 3/1957 | Hook et al. | 260/455 |
| 3,356,702 | 12/1967 | Farmer et al. | 260/429 |
| 3,471,404 | 10/1969 | Myers | 252/45 |
| 3,509,051 | 8/1964 | Farmer et al. | 252/33.6 |
| 3,890,363 | 6/1975 | Malec | 260/455 A |
| 4,098,705 | 7/1978 | Sakurai et al. | 252/33.6 |
| 4,178,258 | 12/1979 | Papay et al. | 252/33.6 |
| 4,204,969 | 5/1980 | Papay et al. | 252/45 |

FOREIGN PATENT DOCUMENTS 1369163 10/1974 United Kingdom .

OTHER PUBLICATIONS

Hotten, B. W., Sulfurized Sperm Whale Oil History, Chemistry, Functions, *NLGI Spokesman*, vol. 37, No. 5, pp. 174–177, 1973.

*Primary Examiner*—Helen M. S. Sneed
*Attorney, Agent, or Firm*—Rasma B. Balodis

[57] ABSTRACT

This invention relates to synergistic antiwear compositions comprising a sulfurized molybdenum dialkyldithiocarbamate and an organic sulfur compound selected from the group consisting of dithiocarbamate acid esters, sulfurized oils and polysulfurized olefins. Lubricating compositions containing the synergistic compositions possess good antiwear properties and improved extreme pressure and oxidation stability.

10 Claims, No Drawings

ORGANOMOLYBDENUM BASED ADDITIVES AND LUBRICATING COMPOSITIONS CONTAINING SAME

BACKGROUND OF THE INVENTION

This invention concerns improved lubricating compositions having multifunctional properties. Another aspect of the invention relates to addition compositions which impart antiwear and antiscuffing properties to lubricating compositions and improve resistance to oxidation and extreme pressure.

The useful life of nearly all automotive and industrial engines is limited by the decrease in size of important engine parts due to wear. This occurs by removal of metal from surfaces by mechanical or chemical attack. To minimize friction and wear, various antiwear additives have been added to lubricants to produce a protective surface film on the metal parts. However, the antiwear lubricants may exhibit other unsatisfactory lubricating characteristics such as deterioration due to oxidation under high temperature conditions and subsequently may have to be formulated with supplemental lubricating additives to prevent such detrimental effects.

It is known that sulfurized molybdenum dihydrocarbyldithiocarbamates possess antiwear properties as well as other desirable lubricating characteristics as disclosed in U.S. Pat. No. 3,356,702 granted Dec. 5, 1967; U.S. Pat. No. 3,509,051 granted Apr. 28, 1970; U.S. Pat. No. 4,098,705 granted July 4, 1978.

Surprisingly, it has been now discovered that sulfurized molybdenum dialkyldithiocarbamates produce a synergistic antiwear effect in combination with certain organic sulfur compounds. Moreover, these combinations possess excellent oxidation inhibiting and extreme pressure properties when incorporated into lubricants.

SUMMARY OF THE INVENTION

According to the invention, there are provided synergistic antiwear compositions comprising:
(1) an organomolybdenum compound of the formula:

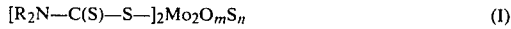

$$[R_2N-C(S)-S-]_2Mo_2O_mS_n \quad (I)$$

wherein R represents alkyl,
m = 2.35 to 3,
n = 1.65 to 1,
m+n = 4; and
(2) an organic sulfur compound selected from the group consisting of:
(a) esters of dithiocarbamic acid of the formula:

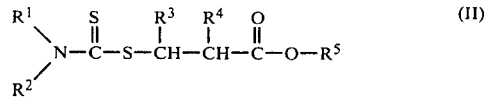

$$\begin{array}{c} R^1 \\ \phantom{R^1} \diagdown \\ \phantom{R^1} \phantom{\diagdown} N-\overset{S}{\underset{\|}{C}}-S-\overset{R^3}{\underset{|}{C}H}-\overset{R^4}{\underset{|}{C}H}-\overset{O}{\underset{\|}{C}}-O-R^5 \\ \phantom{R^1} \diagup \\ R^2 \end{array} \quad (II)$$

wherein $R^1$, $R^2$ and $R^5$ represent alkyl groups having 1 to 18 carbon atoms, $R^3$ represents H and —C-(O)—O—$R^5$ and $R^4$ represents H and methyl;
(b) sulfurized oil and
(c) polysulfurized olefin containing about 40 to 60 percent sulfur and wherein the ratio of the molybdenum compound to the sulfur compound is about 1:4 to about 4:1.

Another aspect of the invention concerns lubricating compositions having improved lubricating properties and comprising a major portion of an oil of lubricating viscosity and about 0.1 to 10.0 percent by weight of a composition comprising an organomolybdenum compound of formula I and an organic sulfur compound selected from the group consisting of esters of dithiocarbamic acid of formula II, sulfurized oil and polysulfurized olefins.

DETAILED DESCRIPTION OF THE INVENTION

The molybdenum component of the present invention is prepared by reacting molybdic oxide and secondary alkylamine with carbon disulfide under controlled temperture conditions. The preferred ratio of carbon disulfide to molybdenum to amine is 2.1:1:1.6. The reaction is characterized by evolution of carbon dioxide as the reaction temperature is increased.

The products obtained are mixed complexes having a symmetrical dithiocarbamate or a mixed asymmetrical dithiocarbamate and thiocarbamate structure essentially similar to the molybdenum compounds described in U.S. Pat. No. 3,509,051 incorporated herein by reference. The molecular formula of the mixed complexes falls within the range of the formula I hereinabove.

The dithiocarbamic acid esters of formula II may be prepared by the method described in U.S. Pat. No. 2,786,866 granted Mar. 26, 1957.

Sulfurized oils may be prepared by treating natural or synthetic unsaturated esters or glycerides with sulfur by known methods as for example in U.S. Pat. No. 2,719,066 granted Nov. 7, 1939. Preferred oils include, among others, lard oil, carboxylic acid esters derived from aliphatic alcohols and fatty acids or aliphatic carboxylic acids, specifically, myristyl oleate and oleyl oleate. Particularly preferred are sperm whale oil and synthetic sperm whale oil substitutes described in German Offen. No. 2,307,600 published Oct. 4, 1973 and incorporated herein by reference.

Various polysulfurized olefins can be used for purposes of the invention. Particularly preferred are polysulfurized olefins containing 40 to 60 percent sulfur. The polysulfurized products may be prepared by reacting sulfur monochloride with an olefin and subsequently, with an alkali metal monosulfide and free sulfur by the method described in U.S. Pat. No. 3,471,404 and incorporated herein by reference. Preferred are products of lower olefins having 2 to 5 carbon atoms.

The sulfur compounds are known to possess certain lubricating properties such as oxidation and corrosion inhibition in various lubricating media. For example, sulfurized sperm oil is known for its oxidative and thermal stability. However, the sulfur compounds alone do not provide adequate antiwear protection for various heavy duty applications of many industrial and automotive lubricants.

Unexpectedly, the sulfur compounds produce synergistic antiwear effect when combined with organomolybdenum compounds in certain ratios. Synergism is displayed by compositions containing about 1 to 4 parts by weight of the sulfur compound to about 4 to 1 part by weight of the molybdenum compound.

The synergistic compositions may be incorporated in any lubricating media by known methods. The compositions impart antiwear as well as oxidation inhibiting and extreme pressure properties to natural and synthetic lubricants formulated as oils or greases.

The base oils employed as lubricant vehicles are typical oils used in automotive and industrial applications such as, among others, turbine oils, hydraulic oils, gear oils and crankcase oils. Petroleum hydrocarbon oils of suitable lubricating viscosity range for example from about 45 SSU at 38° C. about 6000 SSU at 38° C. Typical synthetic oils include ester-type oils such as silicate esters and pentaerythritol esters, hydrogenated mineral oils, silicones and silanes.

The compositions of the invention may be incorporated in the lubricant in an amount effective to produce the desired antiwear characteristics. In many instances, an amount from about 0.1 to 10.0 percent will be sufficient. A preferred range is from about 0.5 to about 3.0 percent by weight of the total lubricant composition.

The lubricating compositions may contain other conventional additives depending on the intended use of the lubricant. For example, formulations may contain rust inhibitors such as metal salts of naphthalenesulfonic acids, sulfur-phosphorus type additives, demulsifiers, dispersants, detergents and the like.

The grease formulations may contain various thickening agents such as, among others, silicate minerals, metal soaps and organic polymers.

The following examples are given for the purpose of illustrating the invention and are not intended in any way to limit the invention. All percentages and parts are based on weight unless otherwise indicated.

1460, 968, medium at 1300, 1218, 1168, weak at 918, 709 and doublet at 1380 and 1365 cm$^{-1}$.

EXAMPLE II

The compositions of the invention were formulated with mineral oil (solvent extracted neutral oil, Sunvis 210 manufactured by Sun Company, Inc.) Sulfurized molybdenum ditridecyldithiocarbamate prepared in Example I was combined with sulfur compounds as indicated in Table I. The sulfurized sperm whale oil substitute contained about 11 percent sulfur (Elco 231 manufactured by Elco Corporation). The polysulfurized olefin prepared by reaction of sulfur monochloride, isobutylene and free sulfur contained 47.0 percent sulfur (Mobilad C-100 manufactured by Mobil Chemical Company).

The compositions were evaluated as synergistic antiwear agents by the 4-Ball Wear Test according to ASTM D 2266 modified for oil samples. The test was conducted at 1800 rpm, 24° C. and load of 20 kg and 40 kg to simulate light and heavy duty applications.

Data compiled in Table I indicate the synergistic performance of the compositions containing molybdenum and sulfur compounds as compared to compositions containing only the individual components. Although sulfurized oil shows adequate antiwear under light duty conditions, its performance under heavy duty conditions is considerably improved in the presence of the molybdenum compound.

TABLE I

| | Compositions, Percent | | | | | | |
|---|---|---|---|---|---|---|---|
| | 1 | 2 | 3 | 4 | 5 | 6 | 7 |
| Components | | | | | | | |
| Mineral Oil | 99.0 | 99.0 | 99.0 | 99.0 | 99.0 | 99.0 | 99.0 |
| Molybdenum Compound | 1.0 | — | 0.2 | 0.5 | 0.8 | — | 0.5 |
| 2-Carbobutoxyethyl diethyldithiocarbamate | — | 1.0 | 0.8 | 0.5 | 0.2 | — | — |
| 1,2-Dicarbobutoxyethyl diethyldithiocarbamate | — | — | — | — | — | 1.0 | 0.5 |
| Physical Properties | | | | | | | |
| 4-Ball Wear, mm | | | | | | | |
| @20 kg | 0.583 | 0.416 | 0.328 | 0.322 | 0.363 | 0.400 | 0.297 |
| @40 kg | 0.677 | 0.724 | 0.500 | 0.439 | 0.512 | 0.700 | 0.429 |

| | Compositions, Percent | | | |
|---|---|---|---|---|
| | 8 | 9 | 10 | 11 |
| Components | | | | |
| Mineral Oil | 99.0 | 99.0 | 99.0 | 99.0 |
| Molybdenum Compound | — | 0.5 | — | 0.5 |
| Sulfurized Oil | 1.0 | 0.5 | — | — |
| Polysulfurized Olefin | — | — | 1.0 | 0.5 |
| Physical Properties | | | | |
| 4-Ball Wear, mm | | | | |
| @20 kg | 0.380 | 0.392 | 0.590 | 0.362 |
| @40 kg | 0.561 | 0.471 | 0.725 | 0.473 |

EXAMPLE I

Molybdic oxide (0.71 moles, 102 grams) and technical grade, 73 percent active ditridecylamine (1.17 moles, 616 grams) were placed in a three-necked, two liter flask equipped with a stirrer, thermometer and reflux condenser. Carbon disulfide (1.5 moles, 114 grams) was added at a controlled rate to maintain reaction temperature at 50° to 55° C. The reaction mixture was maintained at this temperature for one hour, gradually raised to 100° C. and maintained between 100° to 110° C. for 3½ hours. Evolution of carbon dioxide was detected at about 70° C. Water formed during the reaction was removed under vacuum. The yield was 770 grams of a green liquid. The product had an infared spectra characterized by strong absorption peaks at 2900, 1532,

EXAMPLE III

Three percent of 1:1 mixture of molybdenum ditridecyldithiocarbamate and 1,2-dicarbobutoxyethyl diethyldithiocarbamate was formulated with a lubricating grease thickened with lithium 12-hydroxystearate. The extreme pressure performance of the grease was tested by the Timken EP Test, ASTM D 2782. The scar width was 1.7 mm at 45 lbs.

EXAMPLE IV

Three percent of 1:1 mixture of molybdenum ditridecyldithiocarbamate and 1,2-dicarbobutoxyethyl diethyldithiocarbamate was added to SAE 90W gear oil base. The extreme pressure performance of the oil was tested by the Timken EP Test, ASTM D 2782. The scar width was 1.6 mm at 45 lbs.

EXAMPLE V

One percent of 1:1 mixture of molybdenum ditridecyldithiocarbamate and 1,2-dicarbobutoxyethyl diethyldithiocarbamate was added to mineral oil (Sunvis 210). The oxidation stability of the oil was tested by the rotary bomb oxidation test at 150° C. according to ASTM D 2272. The base oil failed the test in less than 50 minutes, while the oil containing the composition of the invention did not show deterioration after 160 minutes.

The above results demonstrate that the compositions of the invention are not only synergists with respect to antiwear performance, but also impart good extreme pressure and oxidation stability to lubricating compositions.

We claim:

1. A synergistic antiwear composition comprising:
(1) an organomolybdenum compound of the formula:

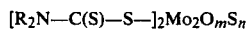

wherein R represents alkyl,
m = 2.35 to 3,
n = 1.65 to 1,
m+n = 4; and
(2) an organic sulfur compound of the formula:

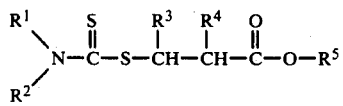

wherein
$R^1$, $R^2$ and $R^5$ represent alkyl groups having 1 to 18 carbon atoms,
$R^3$ represents H and $-C(O)-O-R^5$, and
$R^4$ represents H and methyl;
and wherein the ratio of the molybdenum compound to the sulfur compound is about 1:4 to about 4:1.

2. A composition according to claim 1 wherein the sulfur compound is 2-carbobutoxyethyl diethyldithiocarbamate.

3. A synergistic antiwear composition comprising sulfurized molybdenum ditridecyldithiocarbamate and 1,2-dicarbobutoxyethyl diethyldithiocarbamate in the ratio of about 1:4 to about 4:1.

4. A composition according to claim 2 wherein the ratio is about 1:1.

5. A lubricating composition containing a major amount of an oil of lubricating viscosity and a minor amount sufficient to improve lubricating properties thereof of a multifunctional composition comprising:
(1) an organomolybdenum compound of the formula:

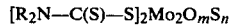

wherein R represents alkyl,
m = 2.35 to 3,
n = 1.65 to 1,
m+n = 4; and
(2) an organic sulfur compound of the formula:

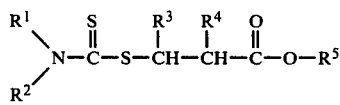

wherein $R^1$, $R^2$ and $R^5$ represent alkyl groups having 1 to 18 carbon atoms, $R^3$ represents H and $-C(O)-O-R^5$, and $R^4$ represents H and methyl; and wherein the ratio of the molybdenum compound to the sulfur compound is about 1:4 about 4:1.

6. A lubricating composition according to claim 5 wherein the multifunctional composition is added in the amount of about 0.1 to 10.0 percent by weight.

7. A lubricating composition according to claim 5 wherein the sulfur compound is 2-carbobutoxyethyl diethyldithiocarbamate.

8. A lubricating composition according to claim 5 which further contains a thickener.

9. A lubricating composition containing an oil of lubricating viscosity and about 0.1 to 10.0 percent by weight of a multifunctional composition comprising sulfurized molybdenum ditridecyldithiocarbamate and 1,2-dicarbobutoxyethyl diethyldithiocarbamate in the ratio of about 1:4 to about 4:1.

10. A composition according to claim 9 wherein the ratio is about 1:1.

* * * * *